United States Patent [19]

Rubin et al.

[11] Patent Number: 4,679,422

[45] Date of Patent: Jul. 14, 1987

[54] METHOD AND APPARATUS FOR STEADY-STATE MEASUREMENT OF LIQUID CONDUCTIVITY IN POROUS MEDIA

[75] Inventors: Jacob Rubin, Palo Alto, Calif.; Dale P. Hammermeister, Las Vegas, Nev.; John R. Nimmo, Mountain View, Calif.

[73] Assignee: The United States of America as represented by the Secretary of the Interior, Washington, D.C.

[21] Appl. No.: 901,360

[22] Filed: Aug. 28, 1986

[51] Int. Cl.[4] .......................................... G01N 15/08
[52] U.S. Cl. ..................................................... 73/38
[58] Field of Search .......................................... 73/38

[56] References Cited

U.S. PATENT DOCUMENTS 3,380,292  4/1968  LeFournier ............................ 73/38
3,683,674  8/1972  Roy ........................................ 73/38

FOREIGN PATENT DOCUMENTS

1153272  4/1985  U.S.S.R. ................................ 73/38
1155912  5/1985  U.S.S.R. ................................ 73/38

Primary Examiner—Stewart J. Levy
Assistant Examiner—Joseph W. Roskos
Attorney, Agent, or Firm—Thomas Zack; E. Philip Koltos

[57] ABSTRACT

In the operation of the present invention, a compacted porous medium is provided with a supply of the desired liquid and is subjected to centrifugal force until the measurement of the flow rate of liquid through the medium is substantially constant. The apparatus comprises: the porous medium in a container and an arrangement of reservoirs which supply liquid to the medium and collect liquid coming out of the medium while maintaining constant pressures at the inflow and outflow ends of the medium. The use of this invention entails measurements of the flow rate of liquid through the medium and conditions of liquid in the medium for the purpose of determine the liquid conductivity.

13 Claims, 8 Drawing Figures

METHOD AND APPARATUS FOR STEADY-STATE MEASUREMENT OF LIQUID CONDUCTIVITY IN POROUS MEDIA

FIELD OF INVENTION

The invention is in the general field of porous media physics. Specifically, the invention measures the liquid permeability of a porous medium, i.e., the property of the medium which expresses how easily liquid flows through the medium under the influence of a driving force. In this description, the term "permeability" refers to the liquid permeability of a porous medium, regardless of what the liquid is or whether it fills the pores completely or partially (with the remaining pore volume filled with gas). It includes the concepts often expressed by terms such as "relative permeability," "hydraulic conductivity" (saturated or unsaturated), and "liquid conductivity."

BACKGROUND OF THE INVENTION

The measurement of permeability is of great importance in several fields which apply the principles of porous-media physics. (1) In hydrology, permeability measurement is important in studies of infiltration, redistribution of water in the unsaturated zone, recharge of aquifers, and groundwater flow within aquifers or across confining layers of aquifers in response to natural or artificially generated pressure gradients. (2) In the petroleum industry, the measurement of permeability of porous rock with oil filling or partly filling its pores is essential in the investigation of oil-bearing rock formations and in the optimum design of oil-extraction systems. (3) In environmental engineering, the permeability of soils, sediments, rocks, clays, and artificial porous media is important in designing and locating toxic waste disposal facilities and in predicting the vulnerability of aquifers to contamination. The objectives here are to isolate the waste to the greatest extent possible, and, if leaks do occur, to minimize the transport of toxic substances to a broader environment. Permeability relates directly to the matter of isolation. It relates indirectly to the transport of dissolved toxic materials, being an essential component of predictive solute-transport models. (4) In agriculture, permeability is important for knowledge of the transport of water in and near the root zone, related to the problems of irrigation and drainage practices as well as of crop and soil management. (5) In soil mechanics, permeability is important as one of the factors that determines the soil water content at a given time and place, which in turn influences the rate of soil consolidation as well as the mechanical properties of the soil related to the question of stability of buildings and other structures.

Previously, the most accurate method of measuring liquid conductivity was by measuring the steady-state flow rate with gravity as the driving force. The weakness of gravitational force means that the measurement takes a long time, prohibitively long when the conductivity is very low. This is the case when pores of the medium are very small (as in fine clays) or, for unsaturated flow, when the liquid of interest occupies only a small fraction of the pore space (as in soils that have been partially drained or dried from a saturated state). Examples of steady-state methods may be seen in the journal Physics, vol. 1, pages 318-333, 1931; and U.S. Pat. No. 2,345,935. Many techniques employing unsteady flow are available for measuring low permeabilities, but the theoretical basis of these methods involves approximations or assumptions due to which the results of the measurements are not very accurate. Examples of these techniques may be seen in Soil Science of America Proceedings 20, pages 458-462, 1956; Soil Science Society of America Proceedings 17, pages 206-209, 1953. The present invention, by permitting substitution of centrifugal force for gravity, reduces the time required for a steady-state measurement, extending the method to finer or less saturated media without a great sacrifice in accuracy. Centrifugation has previously been used in several applications to flow through porous media, but not in connection with steady-state permeability measurements, see for example: U.S. Department of Agriculture Bureau of Soils Bulletin 45, 1907; U.S. Department of Agriculture ARS 41-134, page 8, 1967; Soil Science Society of America Proceedings 3, pages 65-69, 1938; Soil Science Society of America Proceedings 40, pages 212-218. 1976; and AIME Transactions 160, pages 114-123, 1945.

THEORY OF THE PRESENT INVENTION

The purpose of the invention is to measure the liquid permeability of a sample of a porous medium. The invention is applicable to at least two cases of fluid flow through porous media: (1) saturated flow, in which the pores of the medium are completely filled with a single liquid such as water or oil; and (2) unsaturated (or liquid-gas) flow, in which the pores of the medium are partly filled with a liquid, the remaining pore volume being filled with a gas such as air. Consider a porous medium in a centrifugal field with a fixed state of saturation or partial saturation at the bottom and a constant pressure above a porous plate at the top. ("Top" here means the inflow end, closest to the center of rotation and "bottom" the outflow end, farthest away.) Eventually conditions within the medium will stop changing. The flow then is steady, driven in general by two forces (gravity being negligible in this situation): (1) the centrifugal force $bw^2r$, where b is the relative density of the liquid, w is the angular speed of the centrifuge, and r is the radius from the center of rotation to a point in the sample and (2) the gradient of matric potential dp/dr that has developed. The matric potential p is directly related to the degree of saturation of the porous medium, decreasing as the liquid content of the medium decreases. For example, the tendency of water to flow from wetter to drier regions in a water-air system is expressed by saying that it moves from greater to lesser matric potential, or that it is driven by the matric potential gradient. For saturated flow, the matric potential gradient is equal to zero, so only the centrifugal force needs to be considered. Darcy's law, the generally accepted description of fluid flow in porous media, is applied in the form $$q = -K(p)[(dp/dr) - bw^2r]$$

where q is the flux density (volume flow per unit time per unit area) and K is the liquid conductivity. Because K depends on the degree of saturation of the medium it is written here as a function of p. Possible units for quantities in the above equation are as follows: meters (m) for r, radians/second $(s^{-1})$ for w, megagrams/m$^3$ for b, kilopascals (kPa) for p, and m/s for q. The units of K would then be (m/s) (kPa/m), which can be converted to m/s by dividing by g×b, where g is the acceleration of gravity, 9:807 m/s$^2$. The determination of K(p) by this method requires a measurement of q and the two terms of driving force dp/dr and bw$^2$r.

The centrifugal force is easily computed from the quantities b, w, and r, requiring during centrifugation only the measurements needed to verify w and to determine the appropriate value of r. Unlike gravity, this force has a definite spatial dependence, increasing linearly with r from the top to the bottom of the column. Another difference is that water flow in a centrifugal field is subject to coriolis forces and forces due to angular acceleration when the centrifuge starts or stops. These effects, though, can easily be shown to be negligible for the small flow rates encountered in cases where the invention is applicable. Another, more serious problem is the angular divergence of the centrifugal force. Because this force is always directed along a radius of the centrifuge, it is not parallel to the axis of a cylindrical sample at all points. The medium tends to be more nearly saturated and the flux to be greater near certain portions of the outer boundary. If this divergence effect is significant, the overall flux will be greater than for the case where conditions are laterally uniform. It must be shown experimentally that the magnitude of the effect is small for at least some range of rotational speeds.

Knowledge of the p(r) profile is essential for calculation of dp/dr and also for finding the appropriate value of r to be used in calculating bw$^2$r. Experimental measurement of p(r) is required in a measurement of K, but for known K(p), theory can predict this profile because p must assume whatever values make K(p) and dp/dr consistent with the steady-state flow conditions for all values of r. A numerical model has been developed to predict p(r). It shows that for certain coarse media (e.g. Oakley sand) the gradient dp/dr is small and can be neglected in comparison to reasonable values of centrifugal force.

An abstract of this invention was first distributed before an oral presentation on Nov. 29, 1984.

SUMMARY OF THE PRESENT INVENTION

The apparatus of the present invention includes a cylindrical sample of the porous medium with porous plates on the two ends and various reservoirs containing liquid that will flow or has flowed through the sample. This apparatus is put through a series of centrifuge runs until steady-state flow is established. The steady-state condition is verified by two criteria: constant average water content of the sample (inferred from unchanging sample weight) and constant flux through the sample (known from changes in reservoir weights). Measurements and calculations of flux and driving force determine the permeability.

BRIEF DESCRIPTION OF THE DRAWINGS

The apparatus of the present invention and the test results can be seen in the attached drawings wherein.

DETAILED DESCRIPTION OF THE APPARATUS AND METHOD

Figure 1:
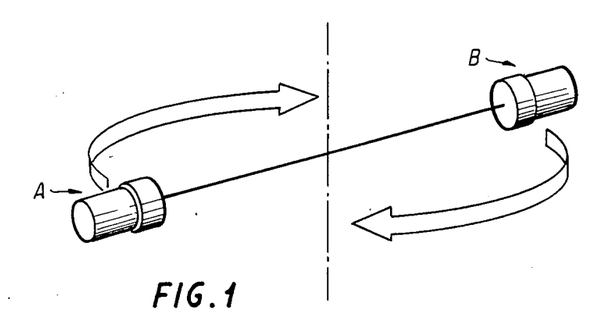
FIG. 1 is a schematic representation of the apparatus spinning in a centrifuge.

FIG. 1 is a schematic representation of the interior of the centrifuge used in the tests of the present invention. To keep the centrifuge rotor balanced, two identical sets of apparatus A and B spin opposite each other.

Figure 2:
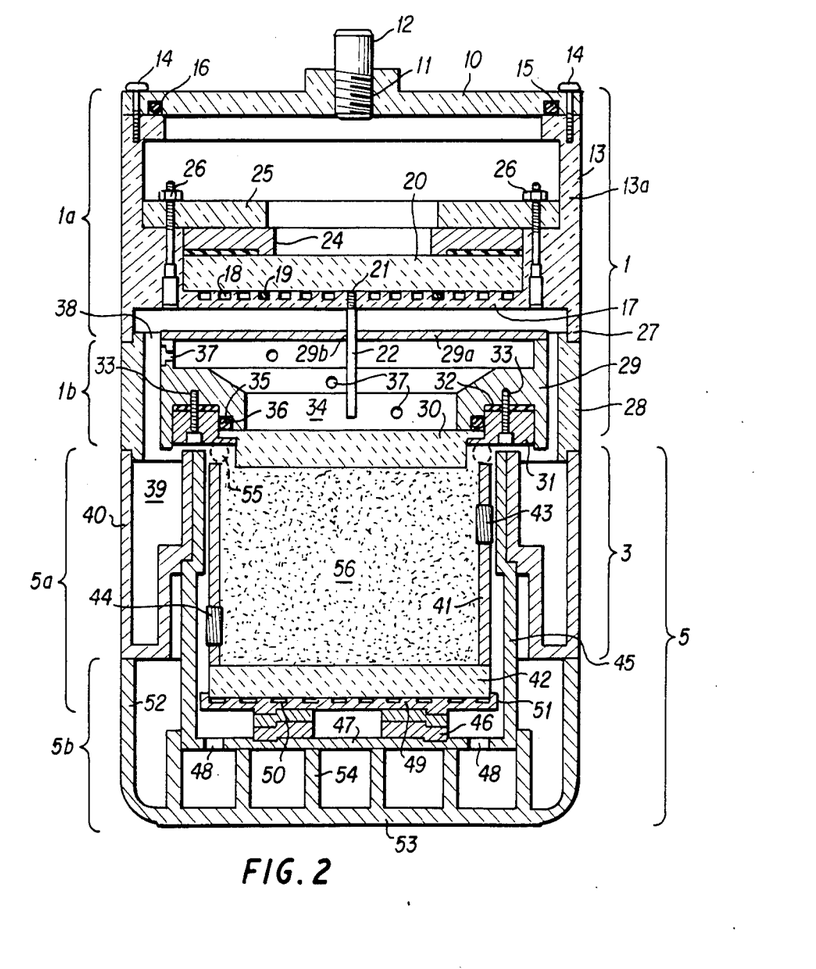
FIG. 2 is a cross sectional view (in the plane of rotation when the apparatus is spinning) of the apparatus of the present invention.
Figure 3:
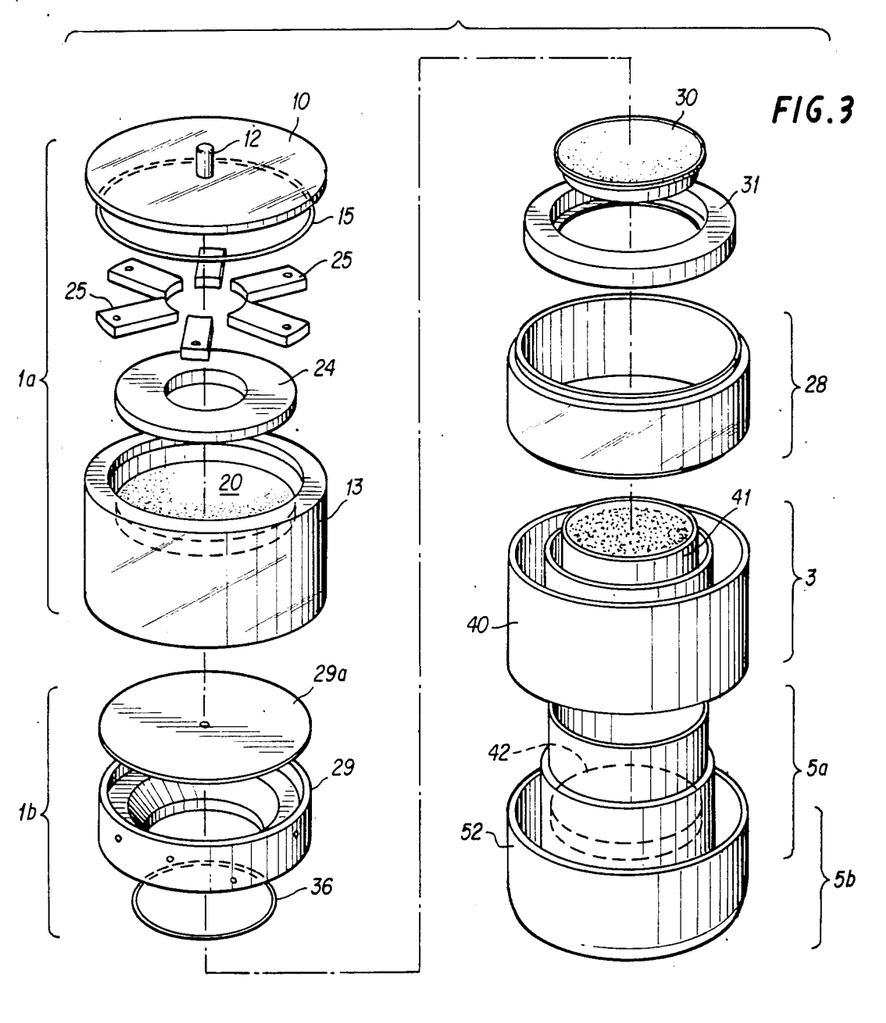
FIG. 3 is an exploded perspective view of the major components of the apparatus.

With reference to FIGS. 2 and 3, the apparatus A of the present invention comprises an upper reservoir assembly 1 which consists of supply reservoir 1a and an upper constant head 1b; the porous medium sample 3; and the lower reservoir assembly 5 which consists of a lower constant head reservoir assembly 5a and a lower overflow reservoir 5b. The assembled components fit into a 1-liter centrifuge bucket for spinning at speeds up to 320 radians/s, with centrifugal forces as great as 2000×g (2000 times the force of gravity) when the medium is about 200 mm from the centrifuge axis.

The supply reservoir assembly 1a comprises in part a top plate 10 having a threaded hole 11 with a plug 12; a cup 13 made of transparent plastic which has secured to it plate 10 by screws 14 in a sealing relationship by an O-ring 15 in circular recess 16 on the undersurface of plate 10. The bottom 17 of cup 13 has a plurality of concentric grooves 18 into a selected one of which is fitted an O-ring 19. The O-ring seals to a porous ceramic disc 20. Liquid flowing out of supply reservoir must pass through this disc, which serves as a controlling flow impedance. The purpose of the plurality of grooves is to provide a choice of the effective area of ceramic through which the liquid passes from the supply reservoir 1a into the upper constant head reservoir 1b, thereby allowing adjustments in the impedance and hence the flow rate. In the center of the bottom 17 is an orifice 21 from which depends a tube 22 which guides the outflowing liquid. On the upper surface of disc 20 is a retainer ring 24, above which are locking tabs 25 which secure disc 20 within cup 13 by a plurality of nuts and threaded studs. Depending from the bottom plate 17 is a circular ring 27 which fits onto the cylindrical spacer ring 28.

The upper constant head reservoir 1b comprises a cup-like ring 29, having a top plate 29a secured thereto, with opening 29b for tube 22 to permit the inflow of liquid from the supply reservoir. A second porous ceramic disc 30 is held onto ring 29 by a retaining ring 31 which is, in turn, fitted into an annular recess 32 on the underside of ring 29 and secured thereto by screws 33. The outside edge surfaces of ceramic disc 30 have a smooth coating of epoxy to prevent leakage of liquid to the lower constant head assembly 5 or the edge of the sample. The permeability of disc 30 determines the degree of unsaturation of the sample; a lower permeability of disc 30 results in a lower flux through the sample and hence a lower permeability and liquid content of the sample. Retaining ring 29 and disc 30 when so mounted form a closed vessel with a porous outflow plate, referred to as the upper constant head reservoir 34. To seal the upper surface of disc 30 to ring 29, an annular recess 35 is formed on the inner under side of ring 29 and an O-ring 36 is fitted therein. To control the head of liquid in reservoir 34, there are provided a plurality of holes 37 with associated plugs at varying heights in the side wall of ring 29. The hole corresponding to the desired head is unplugged. Liquid in excess of the desired head overflows out of this hole into a vertical passageway 38 between spacer ring 28 and ring 29 into upper overflow reservoir 39 which is formed by double-walled circular ring 40. The ceramic plate 20 and O-ring groove 18 in the supply reservoir 1a must be chosen in such a way that the rate of flow into the upper constant-head reservoir 34 exceeds the rate of outflow through the ceramic plate 30, in order that there will always be overflow from the selected hole 37.

The sample 56 is held in a container formed by a cylindrical wall 41 and a third porous ceramic disc 42. The ceramic disc 30 rests on the upper surface of the sample 56 to constitute the only mechanical support of the upper constant-head reservoir 1b, which must be free to move vertically over a certain range in order that slight contractions of the sample 56 will not cause a loss of contact between the sample 56 and the disc 30. The wall 41 has, at different heights, several normally plugged measurement ports, two of which 43 and 44 are shown. With the threaded plugs removed, the measurement ports permit the insertion of electrical resistance probes to measure the water content of the sample during centrifugation, or the use of a more standard, ceramic-tipped tensiometer to measure the matric potential after centrifugation.

The lower constant-head reservoir assembly 5a comprises a cylindrical cup 45 and associated plate 49 and spacers 46. The sample container is inserted into the cup 45. The bottom 47 of the cup 45 has two openings to allow liquid flowing out from the sample to pass through. Disc 42 is fitted into plate 49 which in turn rests upon spacers 46, the plate having on its upper surface a plurality of concentric recesses 50 which in turn are interconnected by radial recesses (not shown) which collect and distribute liquid passing through disc 42. The periphery of plate 49 has an upstanding lip 51 which restrains liquid flowing through disc 42 on the plate until the liquid depth in plate 42 reaches and overflows lip 51 into lower overflow reservoir 5b. The height of lip 51 thus determines the level of the free-water surface within the ceramic plate 42 and hence the negative constant head (suction) applied to the bottom of the sample; a higher lip results in a smaller magnitude of negative head generated in the ceramic disc 42 because of the shorter distance between the top of the lid and the top of the disc. The plates 49 and 42 are held onto the cylinder 41 by means of filament tape. The lower overflow reservoir 5b comprises a cup having a vertical cylindrical wall 52, a bottom 53 and a plurality of segmented ribs 54 upstanding from the bottom 53 (segmentation not shown). The ribs 54 receive and support cup 45 while the reservoir 5b collects the overflow liquid from the lower constant-head reservoir assembly 5a.

When measuring flow through a saturated sample, an O-ring 55 would have to be positioned so as to seal the sample retainer 51 to the edge of the ceramic plate 30 to prevent liquid passing through ceramic disc 30 from leaking laterally into the lower constant-head reservoir assembly 5a. O-ring 55 is not needed when measuring flow through an unsaturated medium because the liquid is at a lower pressure than the surrounding air. It should be understood that when conducting measurements on a saturated medium, the height of lip 51 must be considered in choosing the speed of the centrifuge in order that the liquid pressure at the bottom of the sample would not be low enough to cause desaturation.

Figure 4:
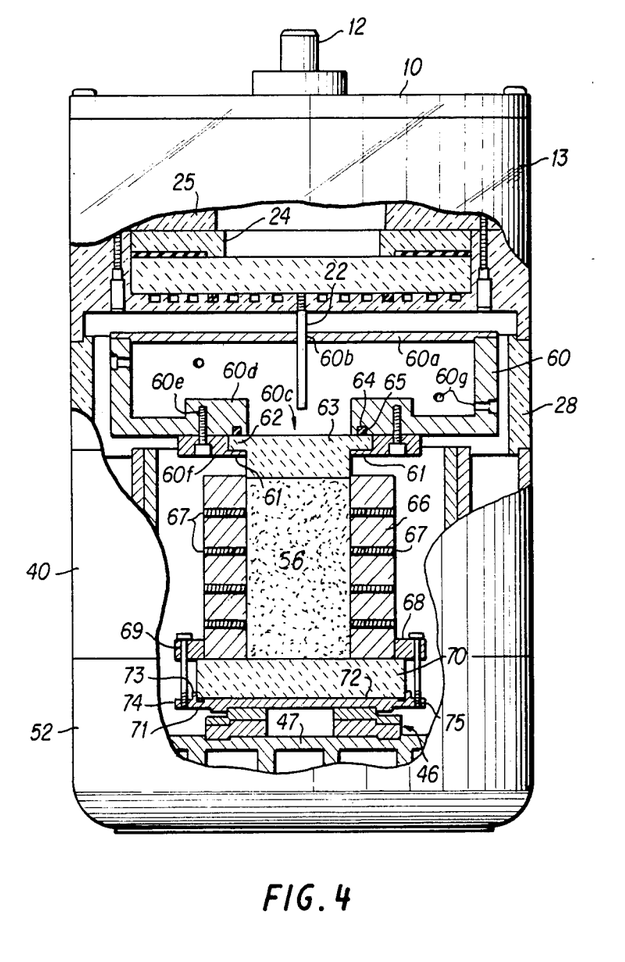
FIG. 4 shows an alternative version of the apparatus for use with small-diameter samples.
Figure 5:
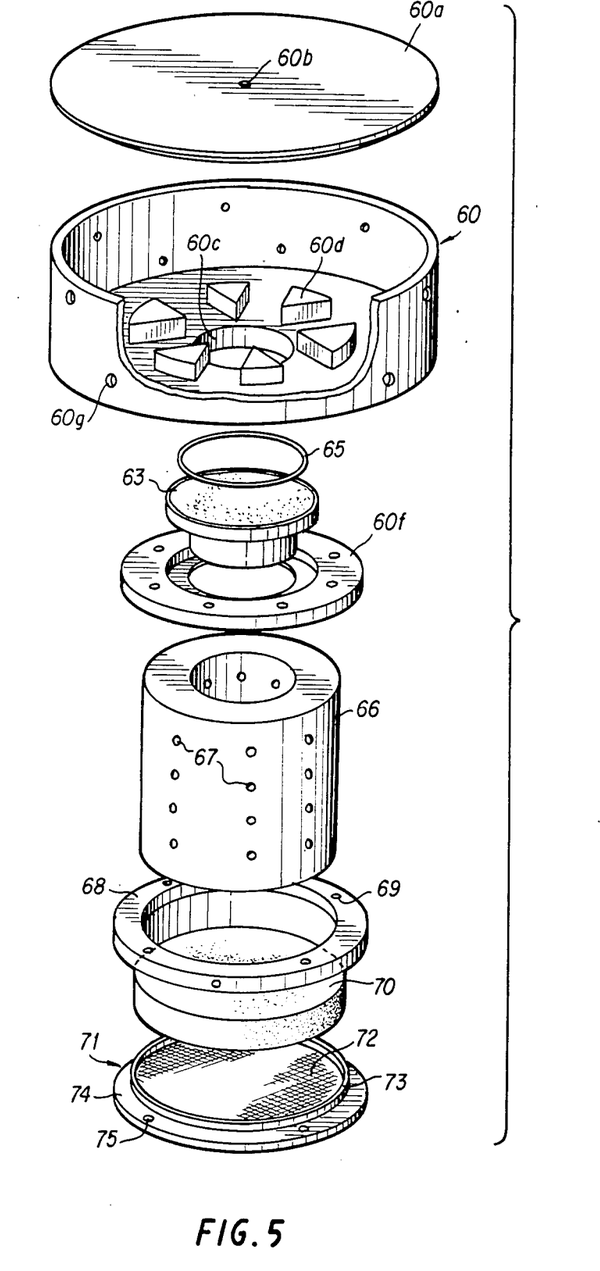
FIG. 5 is an exploded perspective view of the major componenets of the small-diameter apparatus.

FIGS. 4 and 5 depict an auxiliary upper constant-head reservoir, sample container and lower constant-head reservoir for use when the medium whose permeability is to be measured requires or will permit use of a sample of smaller size. This auxiliary unit comprises a cup-like ring 60 having a top plate 60a which has an opening 60b to receive tube 22, central opening 60c around which are a plurality of triangular bosses 60d. Attached to the underside of cup 60 by means of screws 60e which go into blind holes ending inside the bosses 60d, is a retaining ring 60f, which holds the porous ceramic disc 63 onto upper constant-head reservoir 60, by gripping the flange 62. Like 30, disc 63 has an epoxy coating on its edge surfaces. An annular recess 64 in the bottom surface 60g of the cuplike ring 60 holds an O-ring 65 to prevent lateral leakage between the upper surfaces of 63 and the bottom surface of ring 60.

The soil sample retainer comprises a cylindrical wall 66 of greater thickness than wall 41 in FIG. 3. The greater thickness permits the use of various materials, including certain plastics, which are not necessarily as rigid as stainless steel. Additionally, the wall has a plurality of ports 67 which are normally plugged and serve the same purpose as the ports 43 and 44. Further, the retainer wall has fastened to it a collar 68 with holes 69. Wall 66 rests on ceramic disc 70 which in turn rests upon support plate 71. The upper surface 72 of plate 71 is slightly knurled to prevent sealing between the undersurface of disc 70 and the upper surface of plate 71 which might occur if the upper surface of plate 71 were smooth. Plate 71 has an upstanding lip 73 which serves the same purpose as the lip 51. To fasten plates 70 and 71 onto the sample retainer 66, plate 71 has a radically extending collar 74 with a plurality of threaded openings 75 which receive threaded bolts 76 after they have been passed through holes 69 in collar 68. Plate 71 rests on spacer 46.

Figure 6:
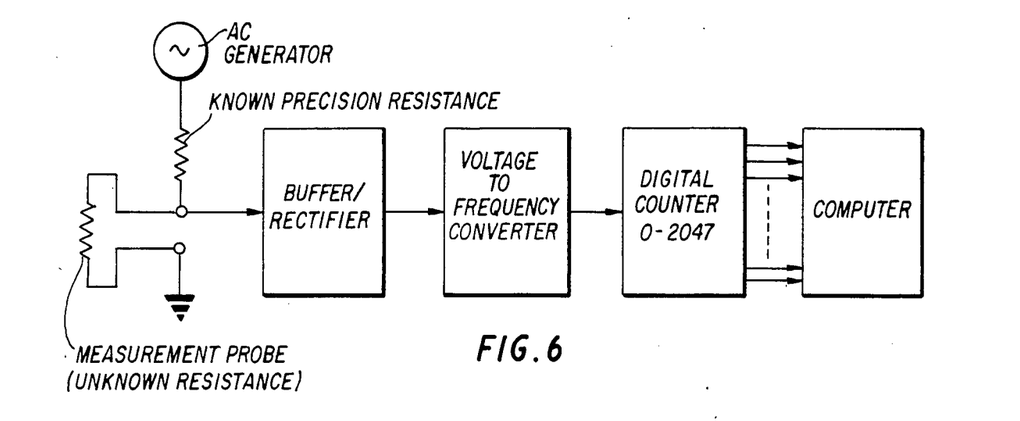
FIG. 6 is a block diagram of the circuit used for electrical resistance measurements as used in determining the moisture state of a point in the sample during centrifugation.

FIG. 6 shows the basic components of the electronic circuit for the measurement of electrical resistance as an indication of liquid content, for use when the liquid is conducting (e.g. water). This system works basically as follows: Two flat nichrome electrodes are placed in direct contact with the sample at one of the measurement ports. The large centrifugal force maintains a firm and steady contact between the electrodes and sample. The battery-powered solid-state circuit, plotted in epoxy for protection against severe mechanical stresses, is put into an adjacent centrifuge bucket and connected by wires to the electrodes. This circuit measures the time-integrated value of sample electrical resistance during a run and records it to be read later when the centrifuge is stopped. The measurement is based on the output of a simple AC voltage divider with the sample resistance as one leg and a precision resistor as the other. The voltage is rectified and applied to a voltage-to-frequency converter, pulses from which drive a digital counter. At the end of a run the counter reading divided by the elapsed time of the run indicates the average frequency and hence the average resistance between the electrodes during the run. This device is calibrated for p as a function of resistance by using it on the sample in the centrifuge without inflow, so that at equilibrium at the position of the electrode probe, p is known independently from the centrifugal-equilibrium formula used by Gardner (Soil Sci. 43: 277,1937) and others.

The cylindrical sample, 50 mm in diameter and about 38 mm high, has porous ceramic plates on both ends for the establishment of boundary conditions. A constant water level is maintained in the reservoir immediately above the ceramic plate that sits on top of the sample (referred to as the "applicator plate"). Liquid is continuously supplied to this reservoir from the reservoir above it at a rate somewhat greater than the flux through the medium. The position of an overflow through a hole in the side of the reservoir determines the height of the water surface above the applicator plate. The pressure just above this plate can be varied by unplugging one of the several overflow holes at various heights. The applicator plate has a conductivity low enough to establish the desired unsaturated condition of the medium.

At the bottom of the sample, a constant matric potential established by means of a free-liquid surface just above the bottom of the lower ceramic plate. This plate sits in a shallow dish; liquid flowing out from the soil accumulates in this dish until it flows over the lip reaching eventually the bottom reservoir. Thus the height of the lip determines the height of the free-liquid surface and hence the matric potential at the bottom of the sample. The capacity of the dish is small (about 0.1 ml) so that when the centrifuge stops, little liquid is available to flow back up into the porous medium.

A steady-state measurement of K starts with a saturated or nearly saturated porous medium. If the medium is particulate, it must have been previously compacted, either in the centrifuge or in its natural setting if that setting entailed a large overburden pressure. The sample is put through a series of centrifuge runs, usually with durations between 15 minutes and 16 hours each. Between runs, the apparatus is weighed to verify and measure the steady-state flow. For this weighing the apparatus is separated into three sections. (1) The porous medium and its container are weighed to determine the average degree of saturation. (2) The upper reservoir assembly, comprising the top (supply) reservoir, the upper constant-head reservoir, and the upper overflow reservoir, is weighed as a unit. The change in weight is taken to indicate the total flux into the medium during the run. (3) Similarly, the bottom reservoirs are weighed for an indication of the flux out of the medium.

Centrifuge runs are repeated until steady-state flow is verified by two criteria: constant average degree of saturation during a run (known from constant sample weight and equality of flux in and flux out) the constant fluxes in two successive runs.

The calculation of K using Darcy's law requires knowledge of the flux density, obtained from the changes in weight of appropriate reservoirs, and also the potential gradients, both centrifugal and matric. The centrifugal gradient is known from the quantities b, w, and r. To determine the matric potential gradient or to verify that it is negligible, p(r) must be measured. This has been done in two ways: (1) by direct measurement using a tensiometer after a centrifuge run, and (2) by measurement of electrical resistance (indicative of wetness and hence p) at a point in the soil during a run. The tensiometer method is basically more accurate, but, unlike the resistance method, it is subject to the effects of moisture redistribution between the end of the run and the time of the measurement.

To use the invention for saturated flow, a minor modification of the instrument is needed. The gap between the top of the sample retainer and the reservoir holding the applicator plate must be sealed with a gasket or O-ring in order to keep liquid from leaking out. (This seal is not needed for unsaturated flow because in unsaturated media the liquid is at a lower pressure than the surrounding air.) In addition, care must be taken in choosing the centrifuge speed and the height of the overflow lip on the lower ceramic plate in order that the liquid pressure at the bottom of the sample is not low enough to cause desaturation. Finally, to prevent bubble formation, it is desirable to make sure the liquid placed in the uppermost reservoir has no dissolved air in it.

The steady-state centrifuge method was successfully applied to water in unsaturated Oakley sand compacted to bulk densities ranging from 1.69 to 1.84 $Mg/m^3$.

The p(r) profiles measured for Oakley sand were nearly uniform, with no measurable gradient detected. In attempts to vary the moisture state of the sample, it was found that changes in the centrifuge speed, the height of water above the applicator plate, and the lower boundary condition had relatively little influence on the profile. Substantial differences in soil water content were obtained only by using applicator plates of different conductivities. This fact and the uniformity of moisture conditions within the sample meant that only one value of K was obtained for each different applicator plate material used.

Figure 7:
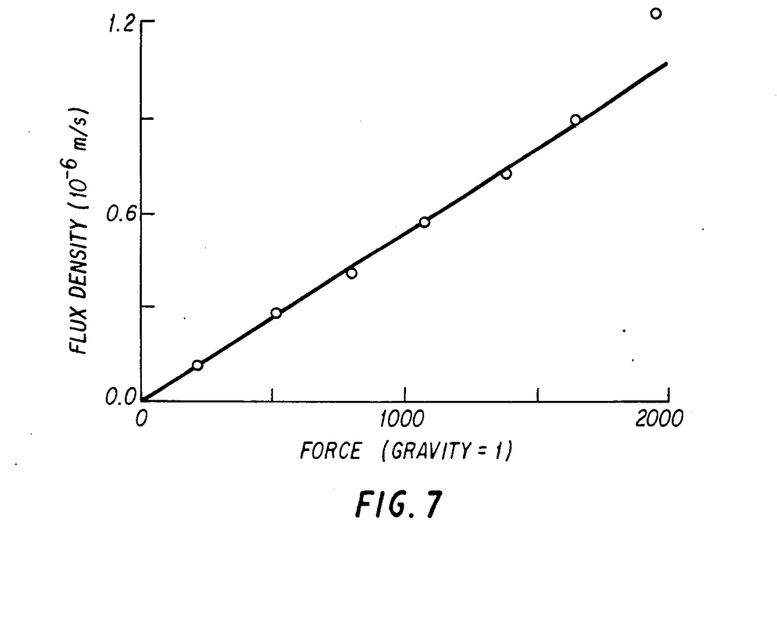
FIG. 7 is graph showing the measured flux density vs. driving force.

The effects of the force divergence were tested with the electrical resistance apparatus. The divergence effects should cause water to accumulate to some extent near points where the perimeter of the sample intersects the plane of rotation. Steady-state runs were performed with the resistance probe placed alternately at the points where the most and least excess moisture was expected. The results indicate a significant difference in the expected direction at centrifugal accelerations of $1900 \times g$ but no significant difference at $200 \times g$. A second check, establishing the range of centrifugal force over which the divergence has little effect on the results, is available by comparing measured fluxes with predictions of Darcy's law. Several measured flux densities are plotted against driving force in FIG. 7. Except at 216 and $1650 \times g$, the points are averages of two or three measurements. For the data at forces of $1650 \times g$ and less, agreement with Darcy's law is very good, as evidenced by the regression line that fits these points with a correlation coefficient 0.9985 and a flux density intercept of $1.83 \times 10^{-9}$ m/s. The flux density at $1950 \times g$ is greater than predicted by the linear fit, but a result of this type is to be expected because the divergence effect is known to be significant for this magnitude of force.

Figure 8:
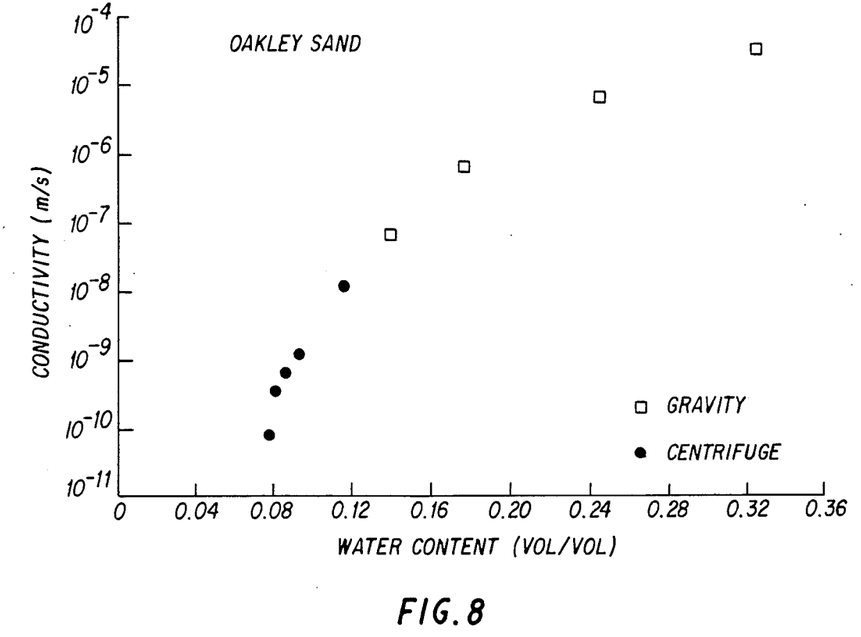
FIG. 8 is a graph showing the measured relation between the water conductivity and the water content of the medium.

Five K-vs.-water-content points obtained using the invention with Oakley sand at bulk density 1.82 $Mg/m^3$ are plotted in FIG. 8 (circular dots). There are five points because five different ceramic materials were available which were usable as applicator plates. The time required to establish steady-state flow and make the measurements required for determination of K and water content varied from about 6 hours for the largest K values to about 30 hours for the smallest. The measurements compare favorably with results from the gravity-driven steady-state method (open squares) applied to essentially the same soil packed to a somewhat lower bulk density.

The overall measurement error, computed by combining estimated measurement errors on each type of primary data (time, balance readings, etc.), is ±2% for water content and ±7% for K.

The lowest K value measured, $7.59 \times 10^{-11}$ m/s, probably does not represent the ultimate limit of the steady-state centrifuge technique. When this measurement was done, the only limiting experimental limitation was the availability of suitable low-conductivity ceramic applicator plates.

The present invention has been described and shown based upon the currently known and available state of the art for the mechanics and electronics involved. It is to be understood and accepted that advances and improvements in either or both of these aspects of the invention are within the scope of the invention as recited in the appended claims.

What is claimed is:

1. A method for establishing and measuring the steady-state flow of a liquid through a unsaturated porous medium and determining the medium's liquid conductivity comprising the steps of:
   (a) placing a compacted sample of the porous medium on which the measurements are to be made on a liquid conducting surface;
   (b) providing for the passing of a continuous supply of a liquid with constant pressures maintained at the liquid inflow and outflow sides of said sample;
   (c) subjecting said sample to a constant centrifugal force;
   (d) collecting the liquid passing through said sample;
   (e) measuring the flow rate of said liquid through said medium and the liquid content of said medium until these measurements are substantially constant over a predetermined time interval; and
   (f) computing the liquid conductivity of said medium from the measurement of said flow rate and the distribution of liquid within said medium.

2. The method according to claim 1 wherein said centrifugal force is in the range of $100 \times g$ to $2000 \times g$.

3. The method according to claim 1 where in step (e) said sample is unsaturated.

4. The method according to claim 1 where in step (e), said measurements are in time intervals which range from 15 minutes to 16 hours, depending on the expected permeability of the sample.

5. An apparatus for measuring the steady-state flow of a liquid through a porous sample medium comprising:
   means for supplying a continuous supply of a liquid to a porous sample medium;
   means for maintaining a substantially constant pressure in the liquid being supplied to the medium;
   means for holding the porous sample medium;
   means for subjecting said sample to a constant centrifugal force as the liquid is supplied thereto;
   means for collecting the liquid and maintaining the liquid at a different substantially constant pressure from the supplied pressure at the point where it has passed through the sample; and
   measuring means for measuring the flow rate of said liquid through said sample and the liquid content thereof based upon the amount of liquid collected therefrom and supplied thereto.

6. A method for establishing and measuring the steady-state flow of a liquid through a porous medium and determining the medium's liquid conductivity comprising the steps of:
   (a) placing a compacted sample of the porous medium on which the measurements are to be made on a liquid conducting surface;
   (b) providing for the passing of a continuous supply of a liquid through said sample;
   (c) subjecting said sample to a constant centrifugal force;
   (d) collecting the liquid passing through said sample;
   (e) measuring the flow rate of said liquid through said medium and the liquid content of said medium by weighing the liquid supplied to the sample, weighing said sample to determine the change of liquid content of said sample, and weighing the collected liquid until these measurements indicate a substantially constant flow rate over a predetermined time interval; and
   (f) computing the liquid conductivity of said medium from the measurement of said flow rate and the distribution of liquid within said medium.

7. A method for establishing and measuring the steady-state flow of a liquid through porous medium and determining the medium's liquid conductivity comprising the steps of:
   (a) placing a compacted sample of the porous medium on which the measurements are to be made on a liquid conducting surface;
   (b) providing for the passing of a continuous supply of a liquid through said sample;
   (c) subjecting said sample to a constant centrifugal force;
   (d) collecting the liquid passing through said sample;
   (e) measuring the flow rate of said liquid through said medium and the liquid content of said medium until these measurements are substantially constant over a predetermined time interval, said constant measurements being established by an unchanging weight of said sample, an unchanging rate of decrease in the weight of said liquid supplied, and a corresponding unchanging rate of increase in the weight of said collected liquid; and
   (f) computing the liquid conductivity of said medium from the measurement of said flow rate and the distribution of liquid within said medium.

8. A method for establishing and measuring the steady-state flow of a liquid through a porous medium and determining the medium's liquid conductivity comprising the steps of:
   (a) placing a compacted sample of the porous medium on which the measurements are to be made on a liquid conducting surface;
   (b) providing for the passing of a continuous supply of a liquid through said sample;
   (c) subjecting said sample to a constant centrifugal force;
   (d) collecting the liquid passing through said sample;
   (e) measuring the flow rate of said liquid through said medium and the liquid content of said medium when said sample is unsaturated, said unsaturated state being established by limiting the rate liquid supplied in accordance with step (b) by first passing the liquid through a second porous medium with a saturated liquid conductivity less than that of the sample porous medium, and second medium being in contact with the sample porous medium until these measurements are substantially constant over a predetermined time interval; and (f) computing the liquid conductivity of said medium from the measurement of said flow rate and the distribution of liquid within said medium.

9. An apparatus for measuring the steady-state flow of a liquid through a porous sample medium comprising:
- means for supplying a continuous supply of a liquid to a porous sample medium, said means comprising a liquid supply reservoir operatively connected to an upper constant head reservoir, said supply reservoir having an adjustable liquid flow controller impedance to regulate the flow rate of liquid to the constant head reservoir;
- means for holding the porous sample medium;
- means for subjecting said sample to a constant centrifugal force as the liquid is supplied thereto;
- means for collecting the liquid after it has passed through the sample; and
- measuring means for measuring the flow rate of said liquid through said sample and the liquid content thereof based upon the amount of liquid collected therefrom and supplied thereto.

10. The apparatus of claim 9 wherein said constant head reservoir has means for controlling the pressure head of the liquid received from the supply reservoir before it passes to the porous medium sample.

11. An apparatus for measuring the steady-state flow of a liquid through a porous sample medium comprising:
- means for supplying a continuous supply of a liquid to a porous sample medium;
- means for holding the sample, said holding means having access means to allow the insertion of electrical resistance probes to measure the water content of the sample during centrifugation;
- means for subjecting said sample to a constant centrifugal force as the liquid is supplied thereto;
- means for collecting the liquid after it has passed by the sample; and
- measuring means for measuring the flow rate of said liquid through said sample and the liquid content thereof based upon the amount of liquid collected therefrom and supplied thereto.

12. The apparatus of claim 11 also including electrical circuitry connectable to probes inserted in said access means to allow the measurement of the time integrated value of the sample's electrical resistance.

13. An apparatus for measuring the steady-state flow of a liquid through a porous sample medium comprising:
- means for supplying a continuous supply of a liquid to a porous sample medium;
- means for holding the porous sample medium;
- means for subjecting said sample to a constant centrifugal force as the liquid is supplied thereto;
- means for collecting the liquid after it has passed by the sample, said means comprising a lower constant head reservoir and an overflow reservoir to collect the overflow liquid therefrom; and
- measuring means for measuring the flow rate of said liquid through said sample and the liquid content thereof based upon the amount of liquid collected therefrom and supplied thereto.

* * * * *